(12) United States Patent
Kurokawa et al.

(10) Patent No.: US 6,207,106 B1
(45) Date of Patent: Mar. 27, 2001

(54) ROOM TEMPERATURE DEODORIZING METHOD BASED ON A POLYMERIZATION REACTION, AN OXIDATION REACTION AND ADSORPTION

(75) Inventors: Tetsuya Kurokawa; Chihiro Kobayashi; Tomonori Tokumoto; Masahiro Yamamoto; Takashi Tsuchida, all of Fukuoka (JP)

(73) Assignee: Toto, Ltd., Fukuoka (JP)

(*) Notice: Subject to any disclaimer, the term of this patent is extended or adjusted under 35 U.S.C. 154(b) by 0 days.

(21) Appl. No.: 09/409,189

(22) Filed: Sep. 30, 1999

Related U.S. Application Data

(62) Division of application No. 08/737,648, filed as application No. PCT/JP96/00748 on Mar. 22, 1996, now Pat. No. 6,010,666.

(30) Foreign Application Priority Data

Mar. 23, 1995 (JP) .................................................. 7-91485

(51) Int. Cl.[7] ........................................................ A61L 9/00
(52) U.S. Cl. .............................................. 422/5; 423/230
(58) Field of Search ............................. 422/4, 5, 120, 422/123, 122, 171, 131; 423/230; 208/246, 249; 95/136

(56) References Cited

U.S. PATENT DOCUMENTS

| | | | |
|---|---|---|---|
| 3,773,044 | * 11/1973 | Wallace | 128/202.22 |
| 4,572,178 | * 2/1986 | Takase et al. | 128/205.27 |
| 5,292,479 | * 3/1994 | Haraga et al. | 422/5 |
| 5,447,551 | * 9/1995 | Huestis et al. | 75/414 |
| 5,568,230 | * 10/1996 | Reddy et al. | 399/100 |
| 5,948,355 | * 9/1999 | Fujishima et al. | 422/5 |
| 5,989,497 | * 11/1999 | Labonte | 422/5 |

FOREIGN PATENT DOCUMENTS

| | | |
|---|---|---|
| 60179125 | 9/1985 | (EP) . |
| 4422173 | 9/1969 | (JP) . |
| 4998763 | 9/1974 | (JP) . |
| 1304232 | 7/1989 | (JP) . |
| 4156854 | 5/1992 | (JP) . |
| 5317392 | 3/1993 | (JP) . |
| 7016465 | 1/1995 | (JP) . |

* cited by examiner

Primary Examiner—Robert J Warden, Sr.
Assistant Examiner—Monzer R. Chorbaji
(74) Attorney, Agent, or Firm—Carrier, Blackman & Associates, P.C.; Joseph P. Carrier; William D. Blackman

(57) ABSTRACT

Hydrogen sulfide is dehydrogenated to generate a HS group and an S group. The HS group is oxidized to generate sulfuric acid, which is bonded to a metal. The S group is polymerized with a $CH_3S$ group to generate methyl trisulfide or methyl tetrasulfide, which is adsorbed to an adsorbent. Methyl mercaptan is dehydrogenated, for example, to generate a $CH_3S$ group. A portion of the $CH_3S$ group is oxidized to generate methanesulfonic acid, which is bonded to a metal. Another portion of the $CH_3S$ group is polymerized with the $CH_3S$ group itself to generate methyl disulfide, at least a portion of which is adsorbed to an adsorbent. Still another portion of the $CH_3S$ group is polymerized with the S group to generate methyl trisulfide or methyl tetrasulfide, which is physically adsorbed to an adsorbent. In this manner, malodor components including hydrogen sulfide and methyl mercaptan can efficiently be removed without producing or release of harmful secondary products. A simple-structure, compact deodorizing apparatus including appropriate metal oxide catalyst and an adsorbent material suitable for achieving the above deodorizing functions is incorporated in a toilet bowl.

12 Claims, 16 Drawing Sheets

WASHED WITH WATER
TWICE
PEAK OF $KMn_8O_{16}$ IS PRESENT

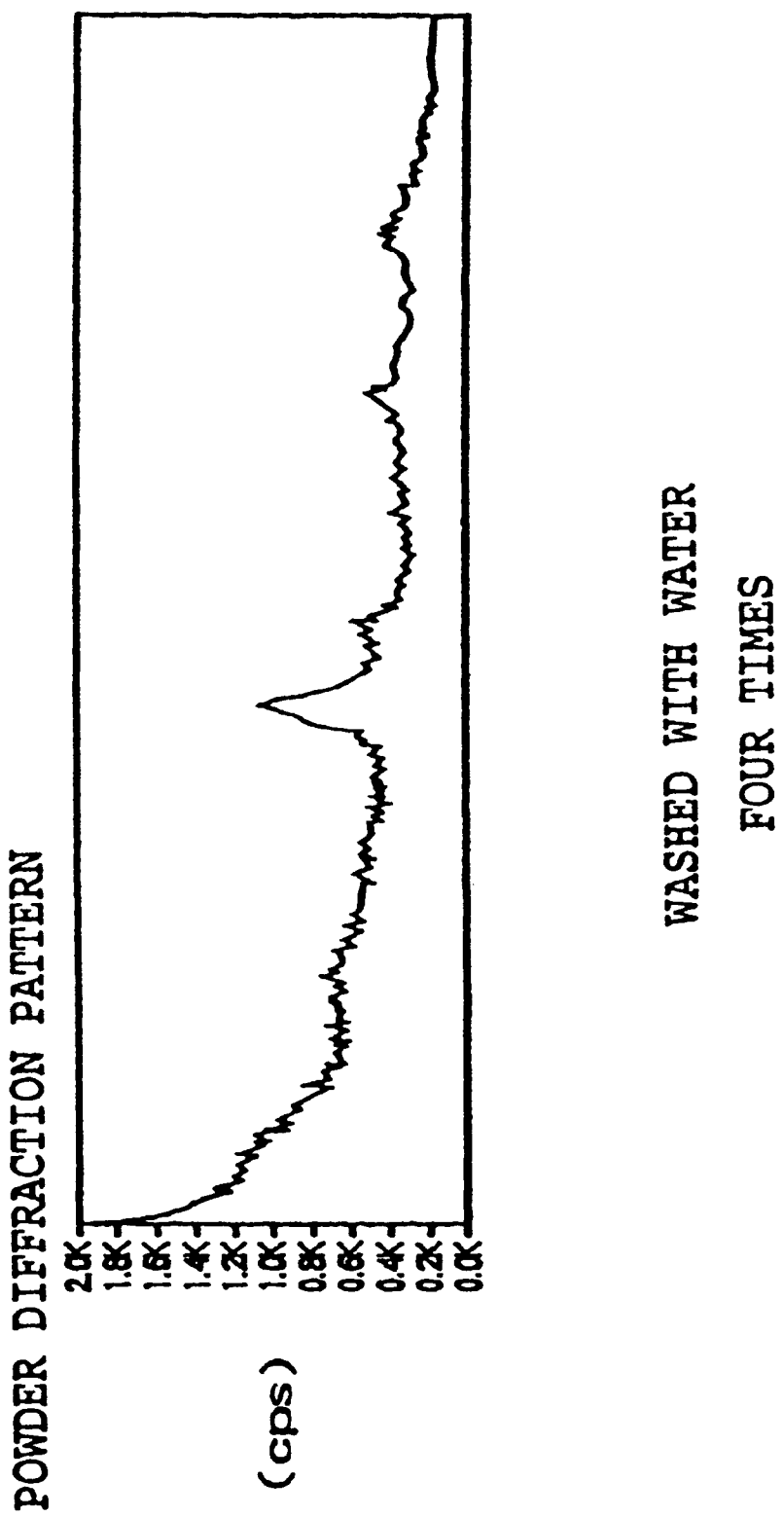

EFFECT OF WATER WASHING ON SPECIFIC SURFACE AREA OF $MnO_2$

XRD PATTERN OF CATALYST OF MnO$_2$ – CuO

BEFORE TOILET WAS USED

WHILE TOILET WAS USED

AFTER TOILET WAS USED

COMPARATIVE RESULTS OF QUESTIONNAIRES ON TOILET SEAT WITH BUILT-IN DEODORIZING FAN AND TOILET SEAT WITH BUILT-IN OZONE DEODORIZING UNIT

- CONSIDERABLY MALODOROUS
- SLIGHTLY MALODOROUS
- MALODOROUS IF CAREFULLY EXAMINED
- NOT MALODOROUS

ROOM TEMPERATURE DEODORIZING METHOD BASED ON A POLYMERIZATION REACTION, AN OXIDATION REACTION AND ADSORPTION

TECHNICAL FIELD

This application is a division of application Ser. No. 08/737/648 filed Nov. 15, 1996 which is a 371 of PCT/JP96/00748 filed Mar. 22, 1996.

BACKGROUND OF THE INVENTION

The present invention relates to a deodorizing method based on a polymerization reaction, an oxidization reaction, and adsorption, a deodorizer composed primarily of a metal oxide which performs a catalytic action, a method of manufacturing such a deodorizer, and a deodorizing apparatus which incorporates such a deodorizer.

BACKGROUND ART

Conventional deodorizing methods include a masking process, an adsorption process, an ozone deodorizing process, and a catalytic process which uses a metal oxide.

The masking process vaporizes and disperses an aromatic liquid or solid for people to lose a sense of odors. The adsorption process employs an adsorbent such as activated carbon or the like to adsorb odor components. The ozone deodorizing process serves to decompose odor components with ozone. According to the catalytic process, odor components are oxidized and modified by the oxidizing capability of a metal oxide which is used.

In the masking process, since the aromatic material is eliminated in a short period of time, it has to be replaced periodically and frequently. The adsorption process needs periodic replacement of the adsorbent because the adsorption capacity thereof is limited.

The ozone deodorizing process is capable of producing a deodorizing effect for a long period of time. However, the ozone deodorizing process is expensive to carry out as it requires an apparatus for generating ozone and a catalyst for decomposing excessive ozone. The catalyst needs to be regenerated by heating or the like. Furthermore, if ozone is generated at a concentration higher than a designed level thereby deactivating the catalyst, then the ozone harmful to human beings is likely to leak out of the deodorizing apparatus. When a sulfur-based odor is to be deodorized by the ozone deodorizing process, a trace amount of toxic gas of $SO_3$ is discharged.

The catalytic process which uses a metal oxide can maintain a deodorizing effect for a long period of time and does not produce hazardous substances. However, the catalytic process may produce other odor components. Specifically, when hydrogen sulfide ($H_2S$) and methyl mercaptan ($CH_3SH$), which are major components of a fecal odor, are brought into contact with a metal oxide such as $MnO_2$ or CuO, the methyl mercaptan is dehydrogenated and dimerized into methyl disulfide ($CH_3$—S—S—$CH_3$) which has a lower odor intensity. However, if methyl disulfide is brought into contact with a metal oxide when both hydrogen sulfide and methyl mercaptan are present, then a polymerization reaction occurs which generates methyl trisulfide ($CH_3$—S—S—S—$CH_3$) and methyl tetrasulfide ($CH_3$—S—S—S—S—$CH_3$). These generated substances are as malodorous as methyl mercaptan, and cannot effectively be deodorized.

SUMMARY OF THE INVENTION

To solve the above problems, a deodorizing method according to the present invention, carries out a polymerization reaction for polymerizing malodor components with each other, an oxidization reaction for oxidizing malodor components, and an adsorption reaction for adsorbing malodor components to an adsorbent, simultaneously or stepwise at normal temperature.

Specifically, for deodorizing hydrogen sulfide ($H_2S$), it is dehydrogenated, for example, to generate an HS group and an S group. The HS group is further oxidized to generate sulfuric acid ($H_2SO_4$), which is bonded to a metal. The S group, obtained through dehydrogenation of methyl mercaptan as discussed below is polymerized with a $CH_3S$ group to generate methyl trisulfide ($CH_3$—S—S—S—$CH_3$) or methyl tetrasulfide ($CH_3$—S—S—S—S—$CH_3$), which is adsorbed to an adsorbent.

For deodorizing methyl mercaptan ($CH_3SH$) simultaneously with the deodorization of hydrogen sulfide ($H_2S$), it is dehydrogenated, for example, to generate a $CH_3S$ group. A portion of the $CH_3S$ group is oxidized to generate methanesulfonic acid ($CH_3SO_3H$), which is bonded to a metal. Another portion of the $CH_3S$ group is polymerized with the $CH_3S$ group itself to generate methyl disulfide ($CH_3$—S—S—$CH_3$), at least a portion of which is adsorbed to an adsorbent. Still another portion of the $CH_3S$ group is polymerized with the S group is discussed above to generate methyl trisulfide ($CH_3$—S—S—S—$CH_3$) or methyl tetrasulfide ($CH_3$—S—S—S—S—$CH_3$), which is physically adsorbed to an adsorbent.

A deodorizer according to the present invention includes a first metal oxide for removing malodor components at normal temperature by being bonded to the malodor components, a second metal oxide for assisting the first metal oxide in its deodorizing action, and an adsorbent for adsorbing the malodor components or products from the malodor components.

The first metal oxide should preferably comprise $MnO_2$ particles of an amorphous nature having a specific surface area of 200 $m^2/g$ or higher. The large specific surface area increases the reaction capability of the first metal oxide. It has been found that CuO is an excellent material for use as the second metal oxide.

Specifically, the deodorizer comprises $MnO_2$ (manganese oxide) particles which have a large specific surface area and are highly active, and CuO (copper oxide) particles which are carried on a surface of powdery or fibrous activated carbon.

Activated carbon such as coconut shell activated carbon or the like is excellent for use as a carrier for carrying the $MnO_2$ particles and also the CuO particles, because the large specific surface area increases the adsorbing capability.

In order to maintain the removal percentage of original odors at a high level, the $MnO_2$ particles and the CuO particles preferably are used in a weight ratio ranging from 8:2 to 4:6.

In order to satisfy the conditions of a high removal percentage of original odors and a low concentration of reaction products, the proportion of the total amount of $MnO_2$ particles and CuO particles to activated carbon is preferably in the range from 4:6 to 6:4 in terms of weight ratios.

A method of manufacturing a deodorizer according to the present invention comprises the steps of reacting a bivalent Mn compound and a septivalent Mn compound with each other, thereafter washing a reaction product with water and filtering the reaction product to produce amorphous $MnO_2$, dispersing the amorphous $MnO_2$ and activated carbon in an aqueous solution of a high concentration of copper salt, neutralizing the aqueous solution with an alkali, filtering and washing a resulting precipitate with water, and then drying the precipitate.

Preferably, the copper salt comprises $CuSO_4$ or $Cu(NO_3)_2$, and the alkali comprises NaOH or an aqueous solution of NaOH.

A deodorizing apparatus according to the present invention comprises a case having an air inlet and an air outlet, a fan housed in the case and rotatable by a motor for discharging air drawn from the air inlet out of the air outlet, and a deodorizer layer disposed on a surface of the fan, the deodorizer layer containing a deodorizer comprising $MnO_2$ (manganese oxide) particles which have a large specific surface area and are highly active, and CuO (copper oxide) particles which are carried on a surface of powdery or fibrous activated carbon. The deodorizing apparatus of the above structure may be incorporated in a toilet bowl.

BRIEF DESCRIPTION OF THE DRAWINGS

FIGS. 10(a)–10(c) are diagrams of XRD patterns showing how the number of water washing cycles affects the specific surface area of $MnO_2$, FIG. 10(a) showing an XRD pattern when the number of water washing cycles is 2, FIG. 10(b) showing an XRD pattern when the number of water washing cycles is 3, and FIG. 10(c) showing an XRD pattern when the number of water washing cycles is 4;

DETAILED DESCRIPTION OF BEST MODE FOR CARRYING OUT THE INVENTION

The present invention will hereinafter be described in detail with reference to the accompanying drawings.

In a deodorizing method according to the present invention, a polymerization reaction for polymerizing malodor components with each other, an oxidization reaction for oxidizing malodor components, and an adsorption reaction for adsorbing malodor components to an adsorbent are carried out simultaneously or stepwise at normal or room temperature.

Figure 1:
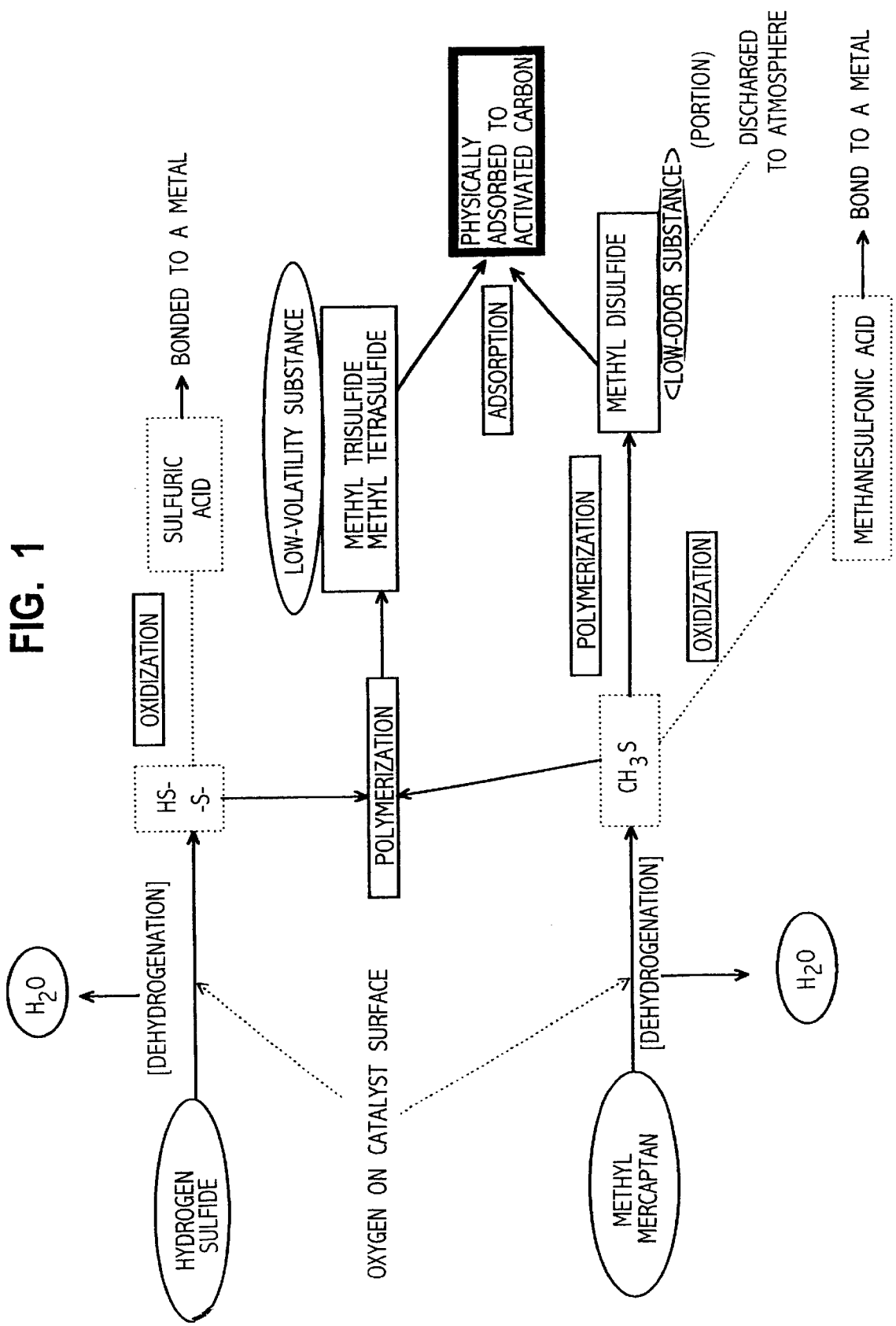
FIG. 1 is a diagram illustrative of a deodorizing method according to the present invention.

FIG. 1 schematically shows the deodorizing method according to the present invention. For deodorizing hydrogen sulfide ($H_2S$), it is dehydrogenated, for example, to generate an HS group and an S group. The HS group is oxidized to generate sulfuric acid ($H_2SO_4$), which is bonded to a metal. The S group is polymerized with a $CH_3S$ group to generate methyl trisulfide ($CH_3$—S—S—S—$CH_3$) or methyl tetrasulfide ($CH_3$—S—S—S—S—$CH_3$), which is adsorbed to an adsorbent.

For deodorizing methyl mercaptan ($CH_3SH$) simultaneously with the deodorization of hydrogen sulfide ($H_2S$), it is dehydrogenated, for example, to generate a $CH_3S$ group. A portion of the $CH_3S$ group is oxidized to generate methanesulfonic acid ($CH_3SO_3H$), which is bonded to a metal. Another portion of the $CH_3S$ group is polymerized with the $CH_3S$ group itself to generate methyl disulfide ($CH_3$—S—S—$CH_3$), at least a portion of which is adsorbed to an adsorbent. Still another portion of the $CH_3S$ group is polymerized with the S group to promote dehydrogenated $H_2S$, generate methyl trisulfide ($CH_3$—S—S—S—$CH_3$) or methyl tetrasulfide ($CH_3$—S—S—S—S—$CH_3$), which is physically adsorbed to an adsorbent.

A deodorizer according to the present invention includes a first metal oxide for removing malodor components at normal temperature by being bonded to the malodor components, a second metal oxide for assisting the first metal oxide in its action, and an adsorbent for adsorbing the malodor components or products from the malodor components.

The first metal oxide should preferably comprise $MnO_2$ particles of an amorphous nature having a specific surface area of 200 m²/g or higher. The large specific surface area increases the reaction capability of the first metal oxide.

Figure 2:
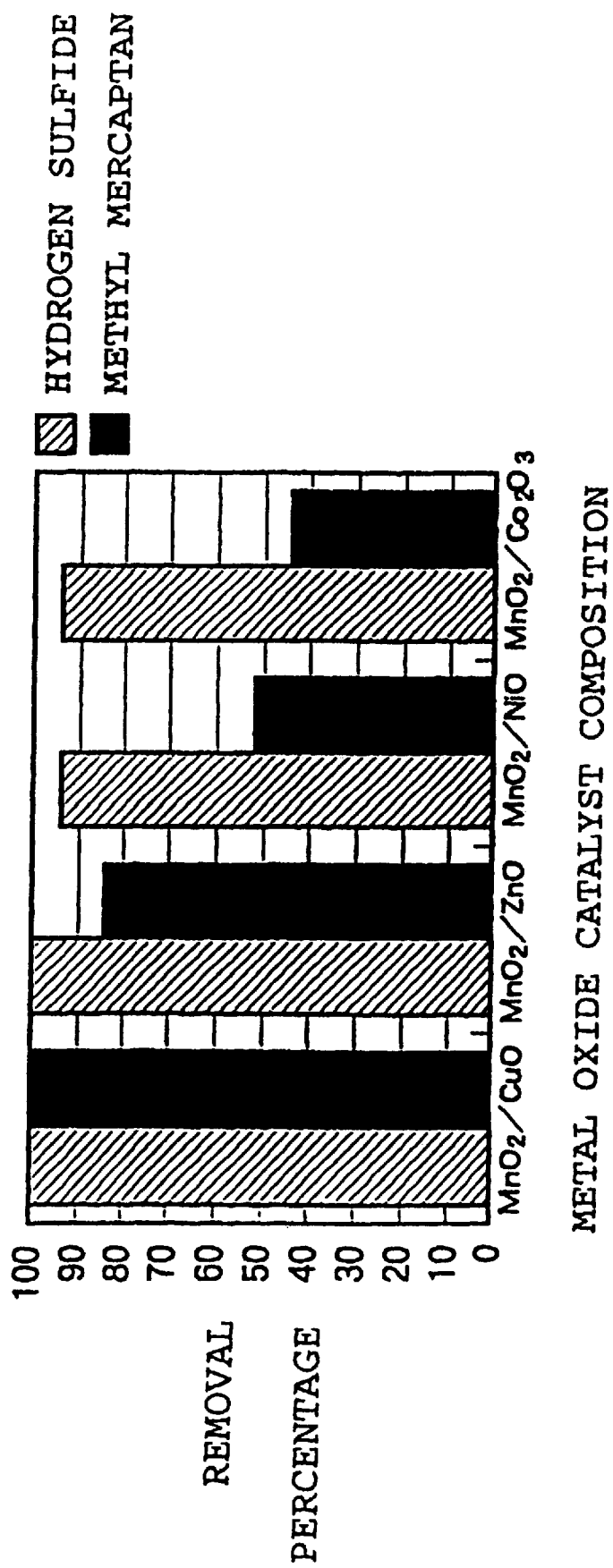
FIG. 2 is a graph showing removal percentages of original odors (hydrogen sulfide and methyl mercaptan) processed using mixtures of $MnO_2$ particles and various second metal oxide particles.

FIG. 2 is a graph showing removal percentages of original odors (hydrogen sulfide and methyl mercaptan) processed using mixtures of $MnO_2$ particles and various second metal oxide particles ($MnO_2$/CuO, $MnO_2$/ZnO, $MnO_2$/NiO, $MnO_2$/$CO_2O_3$). It can be seen from the graph that CuO is excellent for use as the second metal oxide.

Figure 3:
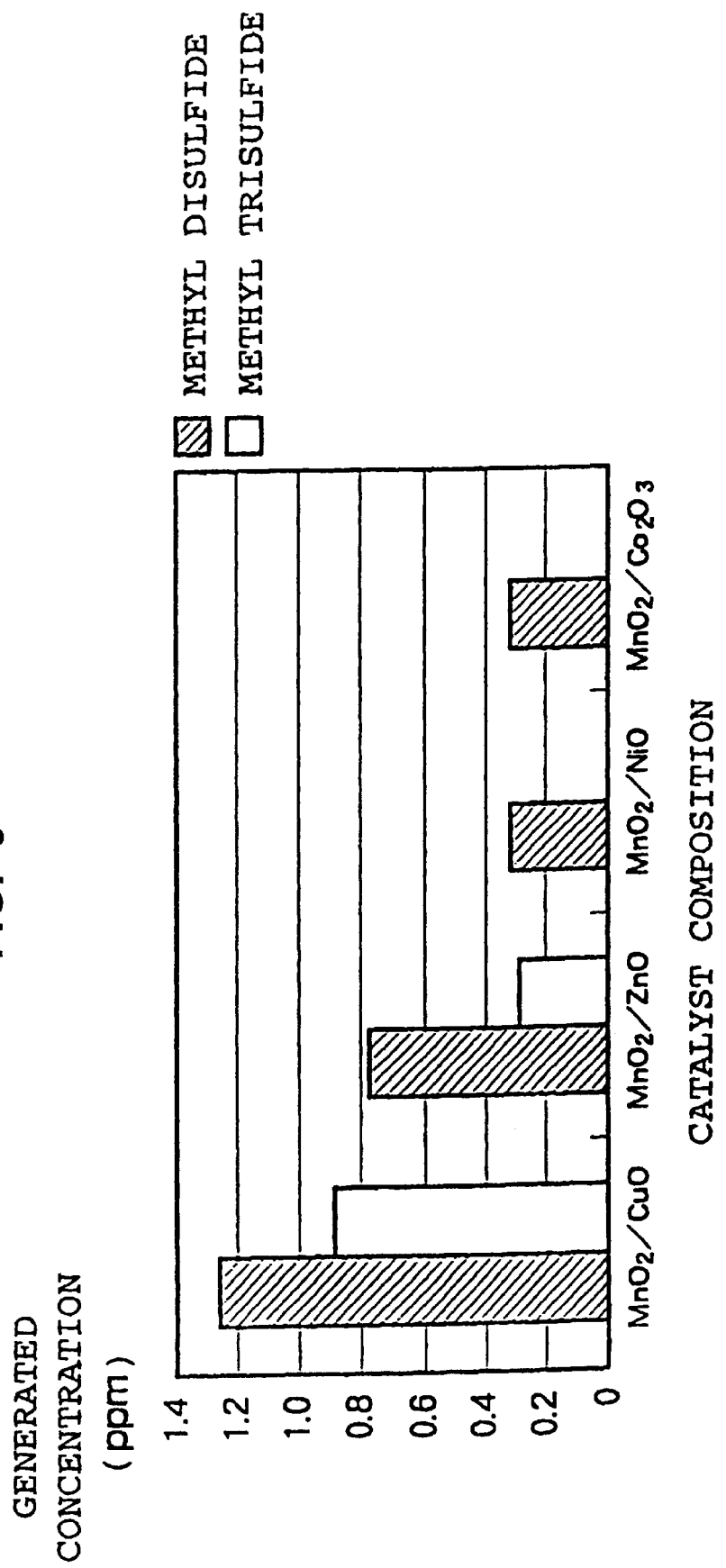
FIG. 3 is a graph showing the results of an analysis of reaction products discharged as outlet gases from a deodorizing apparatus using mixtures of $MnO_2$ particles and various second metal oxide particles.

FIG. 3 is a graph showing the results of an analysis of reaction products discharged as outlet gases from a deodorizing apparatus using mixtures of $MnO_2$ particles and various second metal oxide particles. A study of FIG. 3 indicates that methyl disulfide ($CH_3$—S—S—$CH_3$), etc. is generated by a polymerization of methyl mercaptan with any of the compositions.

Figure 4:
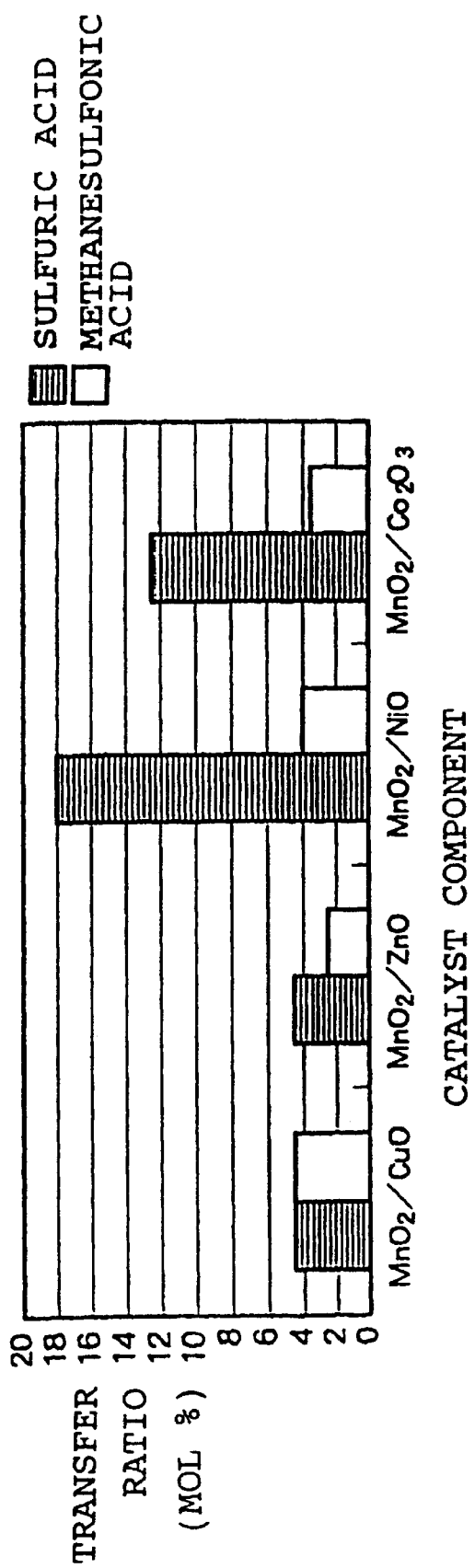
FIG. 4 is a graph showing the results of an analysis of substances remaining on the surface of a deodorizer after malodors were removed using mixtures of $MnO_2$ particles and various second metal oxide particles.

FIG. 4 is a graph showing the results of an analysis of substances remaining on the surface of a deodorizer after malodors were removed using mixtures of $MnO_2$ particles and various second metal oxide particles. A study of FIG. 4 reveals that methanesulfonic acid ($CH_3SO_3H$) is generated with any of the compositions.

It can be understood from the above analyses of the reaction products that a polymerization reaction and an oxidization reaction occur with any of the metal oxide compositions though the reacting weights involved in these reactions vary from each other. Another analysis has confirmed that a harmful gas of SOx is not generated.

With the composition of a mixture of $MnO_2$ particles and CuO particles which exhibits high malodor removal percentages, methyl disulfide and methyl trisulfide which is problematic as a malodor component are generated in large quantities, and it is necessary to adsorb these substances so as not to discharge them out.

Figure 5:
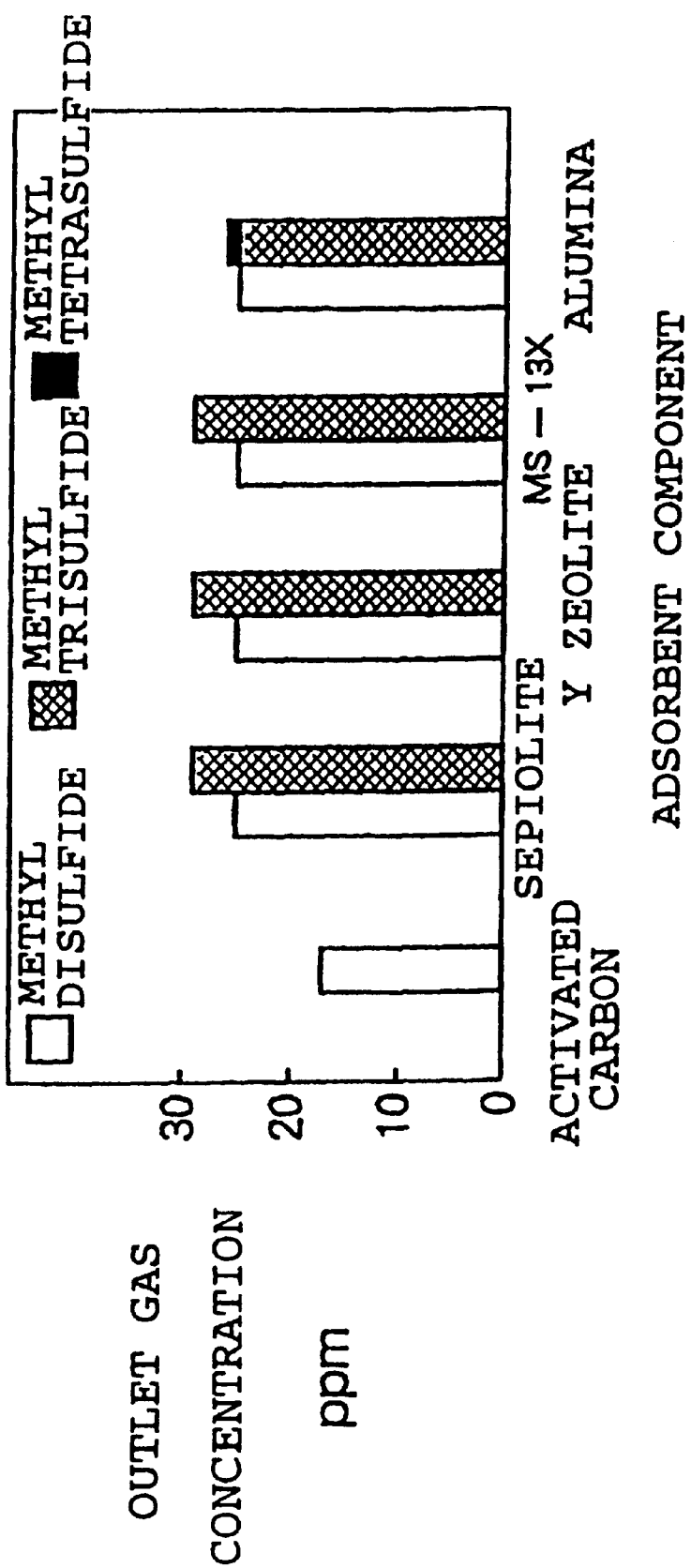
FIG. 5 is a graph showing the results of an analysis of reaction products discharged as outlet gases from a deodorizing apparatus using $MnO_2$ particles and CuO particles carried by various carriers.

FIG. 5 is a graph showing the results of an analysis of reaction products discharged as outlet gases from a deodorizing apparatus using $MnO_2$ particles and CuO particles mixed with various adsorbents. It can be seen from FIG. 5 that activated carbon is an excellent material for adsorbing malodor components to prevent them from being discharged. In particular, activated carbon such as coconut shell activated carbon or the like is excellent for use as a carrier for carrying $MnO_2$ (manganese oxide) particles which have a large specific surface area and are highly active, and also CuO (copper oxide) particles, because the large specific surface area increases the adsorbing capability of the activated carbon. As described above, it is preferable that the $MnO_2$ particles have a specific surface area of 200 $m^2$/g or higher and be substantially amorphous.

Figure 6:
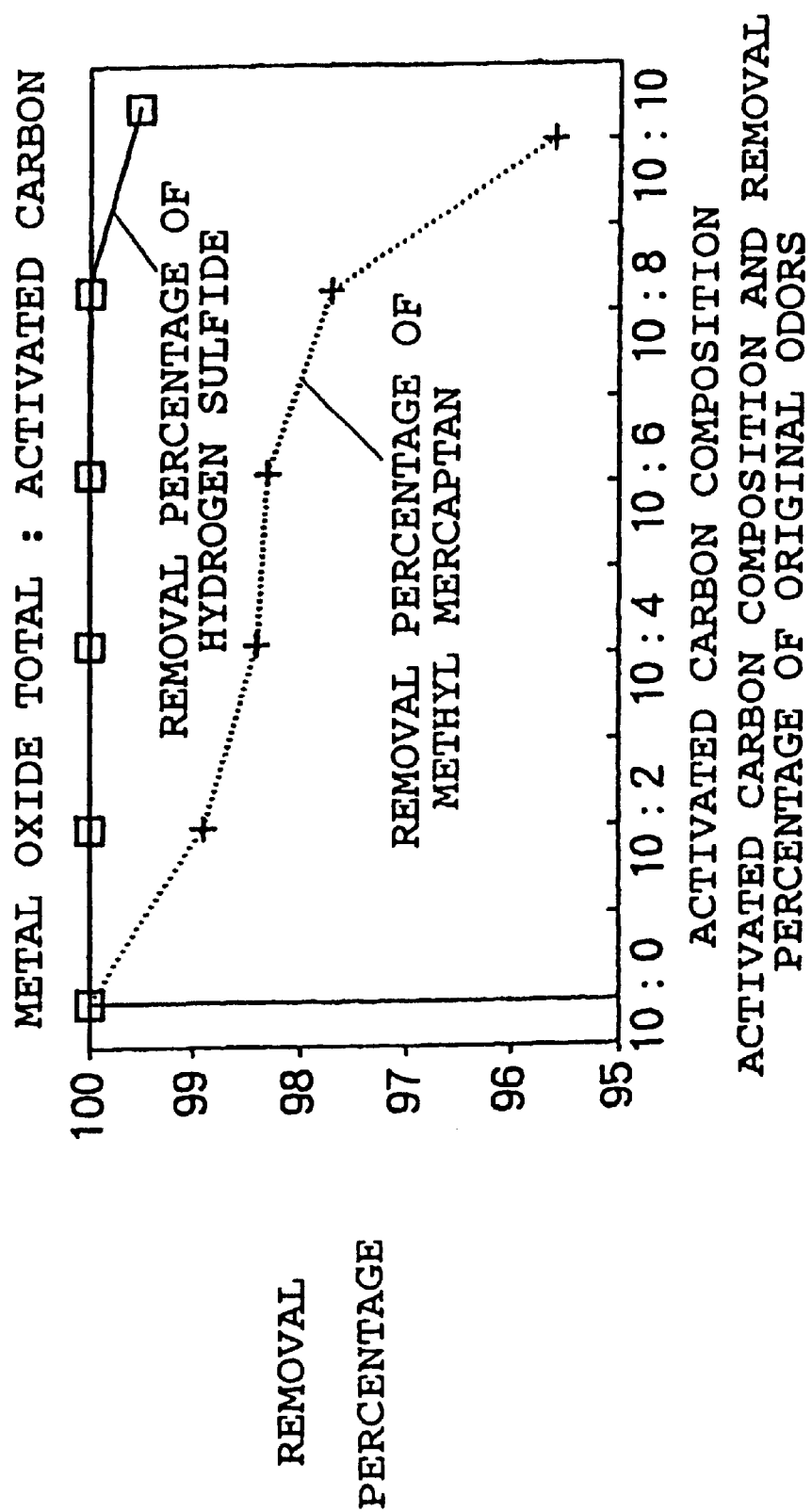
FIG. 6 is a graph showing the relationship between the composition ratio of activated carbon and the removal percentages of original odors (hydrogen sulfide and methyl mercaptan)
Figure 7:
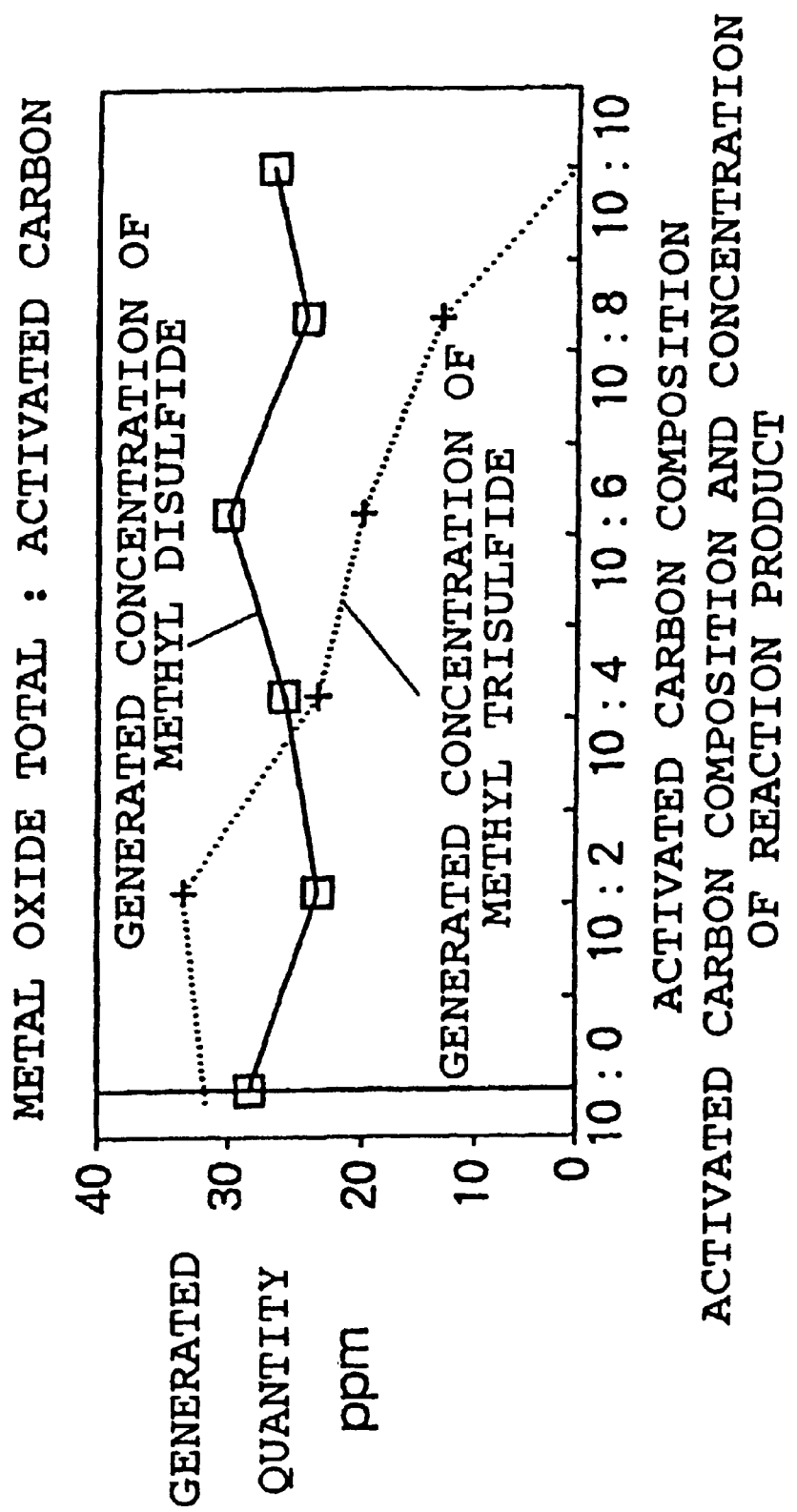
FIG. 7 is a graph showing the relationship between the composition ratio of activated carbon and the concentrations of reaction products (methyl disulfide and methyl trisulfide)

FIG. 6 is a graph showing the relationship between the composition ratio of activated carbon and the removal percentages of original odors (hydrogen sulfide and methyl mercaptan), and FIG. 7 is a graph showing the relationship between the composition ratio of activated carbon and the concentrations of reaction products (methyl disulfide and methyl trisulfide). In order to satisfy the conditions of high removal percentages of original odors and low concentrations of reaction products, it is suitable for the proportion of the total amount of $MnO_2$ particles and CuO particles to activated carbon to be in the range from 4:6 to 6:4 in terms of weight ratios.

Figure 8:
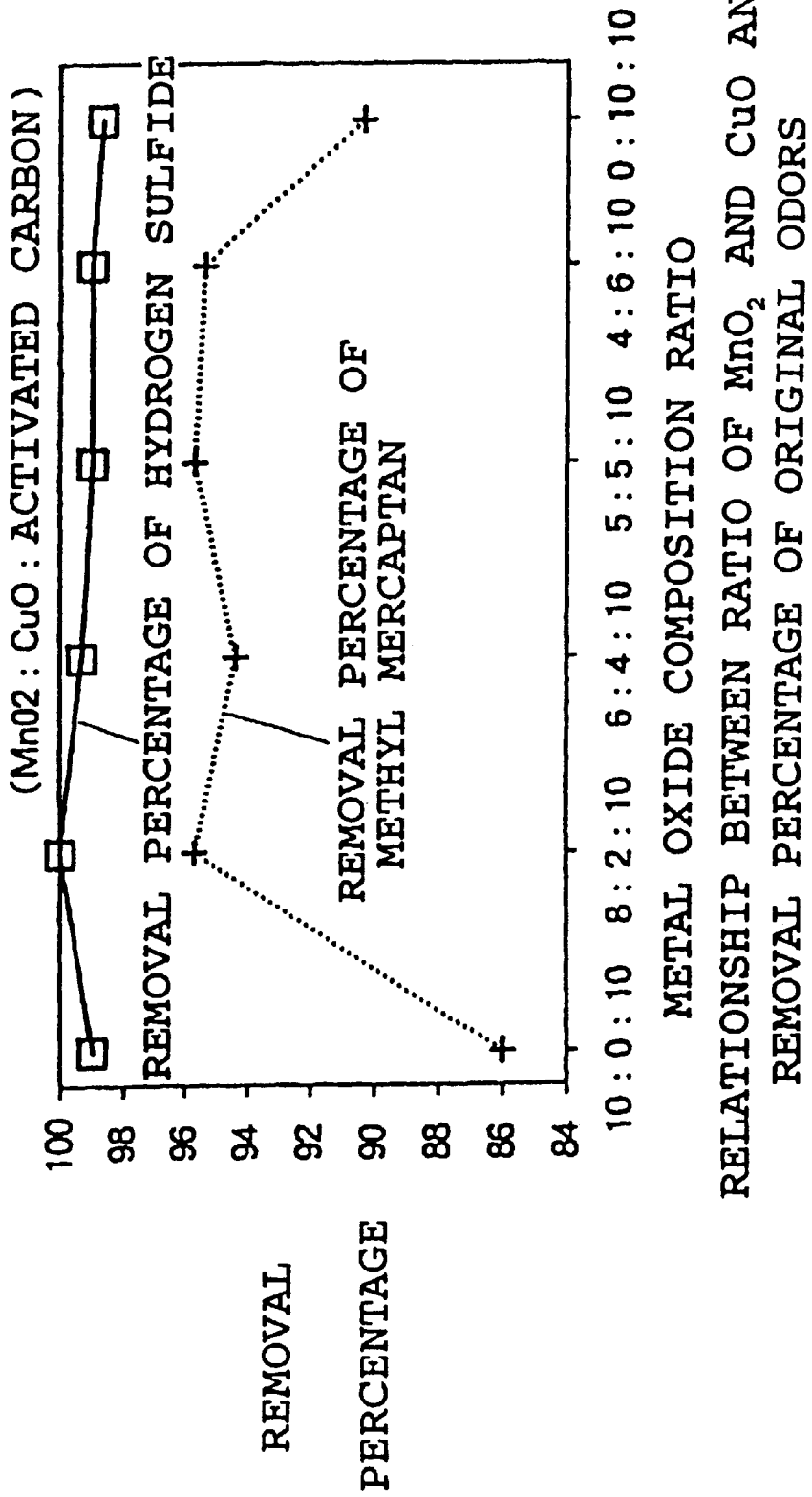
FIG. 8 is a graph showing the relationship between the composition ratios of $MnO_2$ and CuO and the removal percentages of original odors.

FIG. 8 is a graph showing the relationship between the composition ratios of $MnO_2$ and CuO for a given proportion of total metal oxide particles to activated carbon of 1:1, and the removal percentages of original odors. It can be understood from the graph that the weight ratios of $MnO_2$ and CuO should preferably in the range from 8:2 to 4:6 in order to maintain high removal percentages of original odors.

In a method of manufacturing a deodorizer according to the present invention, after a bivalent Mn compound and a septivalent Mn compound are reacted with each other, the reaction product is washed with water and filtered to produce amorphous $MnO_2$, the amorphous $MnO_2$ and activated carbon are dispersed in an aqueous solution of a high concentration of copper salt, then the aqueous solution is neutralized by an alkali, and a precipitate is filtered and washed with water and then dried. In the state of such precipitate, the $MnO_2$ and CuO particles are intimately combined with the activated carbon and carried on the surfaces of the carbon.

In the above method of manufacturing a deodorizer, the copper salt should preferably be $CuSO_4$ or $Cu(NO_3)_2$, and the alkali should preferably be NaOH or an aqueous solution of NaOH.

A deodorizing apparatus according to the present invention has a layer of the deodorizer described above on a surface of a fan for drawing air from an air inlet and delivering the air to an air outlet. Because the deodorizing apparatus is of a simple structure, it can be incorporated in a toilet bowl.

Figure 9:
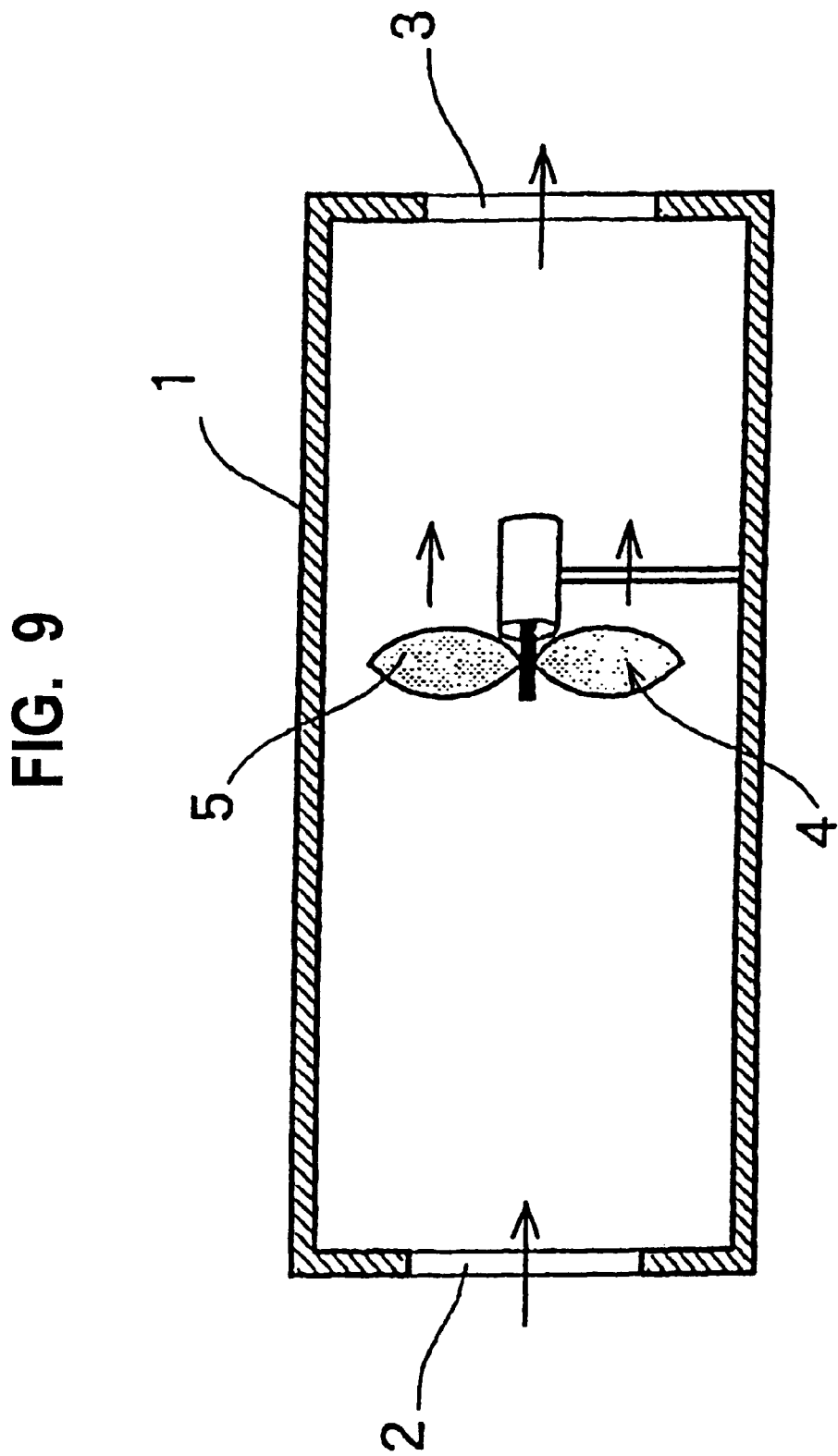
FIG. 9 is a schematic view of a deodorizing apparatus which incorporates a deodorizer according to the present invention.

FIG. 9 shows a specific arrangement of the deodorizing apparatus which incorporates the deodorizer according to the present invention. The deodorizing apparatus comprises a case 1 having an air inlet 2 and an air outlet 3, a fan 4 housed in the case 1 and rotatable by a motor, and a deodorizer layer 5 disposed on a surface of the fan 4, the deodorizer layer 5 comprising the deodorizer according to the above embodiment.

The deodorizer layer 5 is formed by coating and drying a slurry which is produced by kneading the deodorizer with an organic binder. The deodorizer comprises $MnO_2$ particles which have a large specific surface area and are highly active, and CuO (copper oxide) particles which are carried on the surface of activated carbon in the form of a powder or fibers.

Specifically, the method of manufacturing the deodorizer comprises the first step of preparing substantially amorphous $MnO_2$ particles and the second step of carrying the $MnO_2$ particles and the Cu particles on activated carbon.

In the first step of preparing $MnO_2$ particles, a bivalent Mn compound and a septivalent Mn compound are reacted with each other, and thereafter the reaction product is washed with water and filtered to produce amorphous $MnO_2$. More specifically, for example a hydrate of manganese sulfate in an amount corresponding to 0.4 mol of Mn is introduced into 56.8 g of water, and 272 g of 95% sulfuric acid is then gradually introduced into the liquid while stirring the same. Since the liquid generates heat, it is cooled and kept at a temperature ranging from 70 to 75° C. Then, 60 g of potassium permanganate is gradually introduced into the liquid, which is cooled and kept at a temperature ranging from 60 to 65° C. as it generates heat.

The liquid thus obtained, which is of a thick purple color and is highly viscous, is introduced into 10 liters of water. After the solution is washed with water and filtered in four repeated cycles, it is dried at 110° C., producing about 65 g of $MnO_2$ which is of a thick brown color.

Figure 10A:
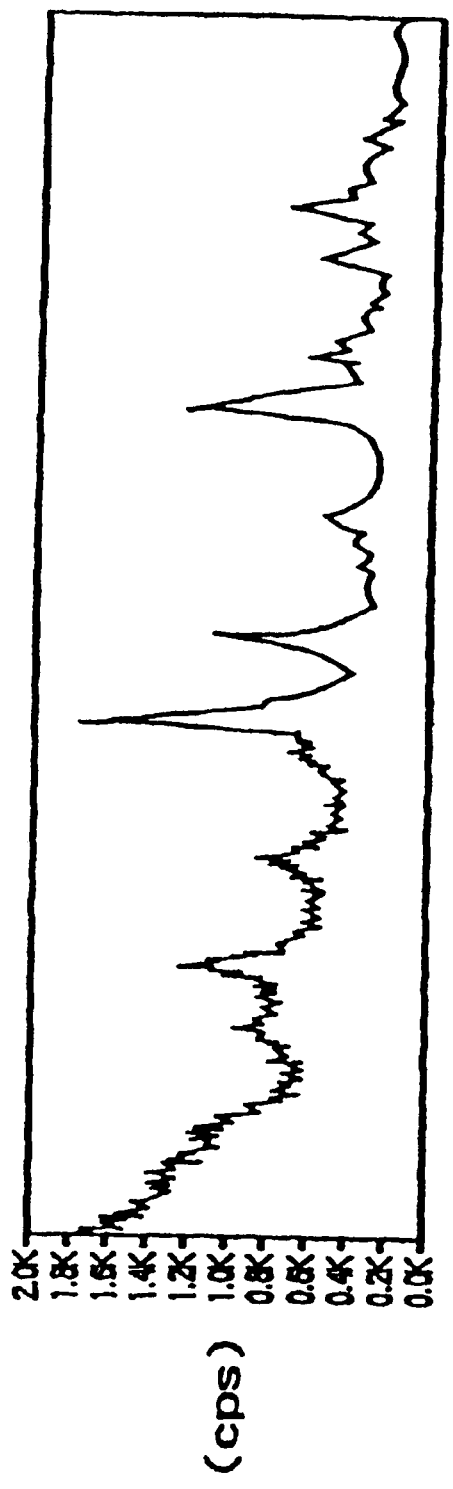
Figure 10B:
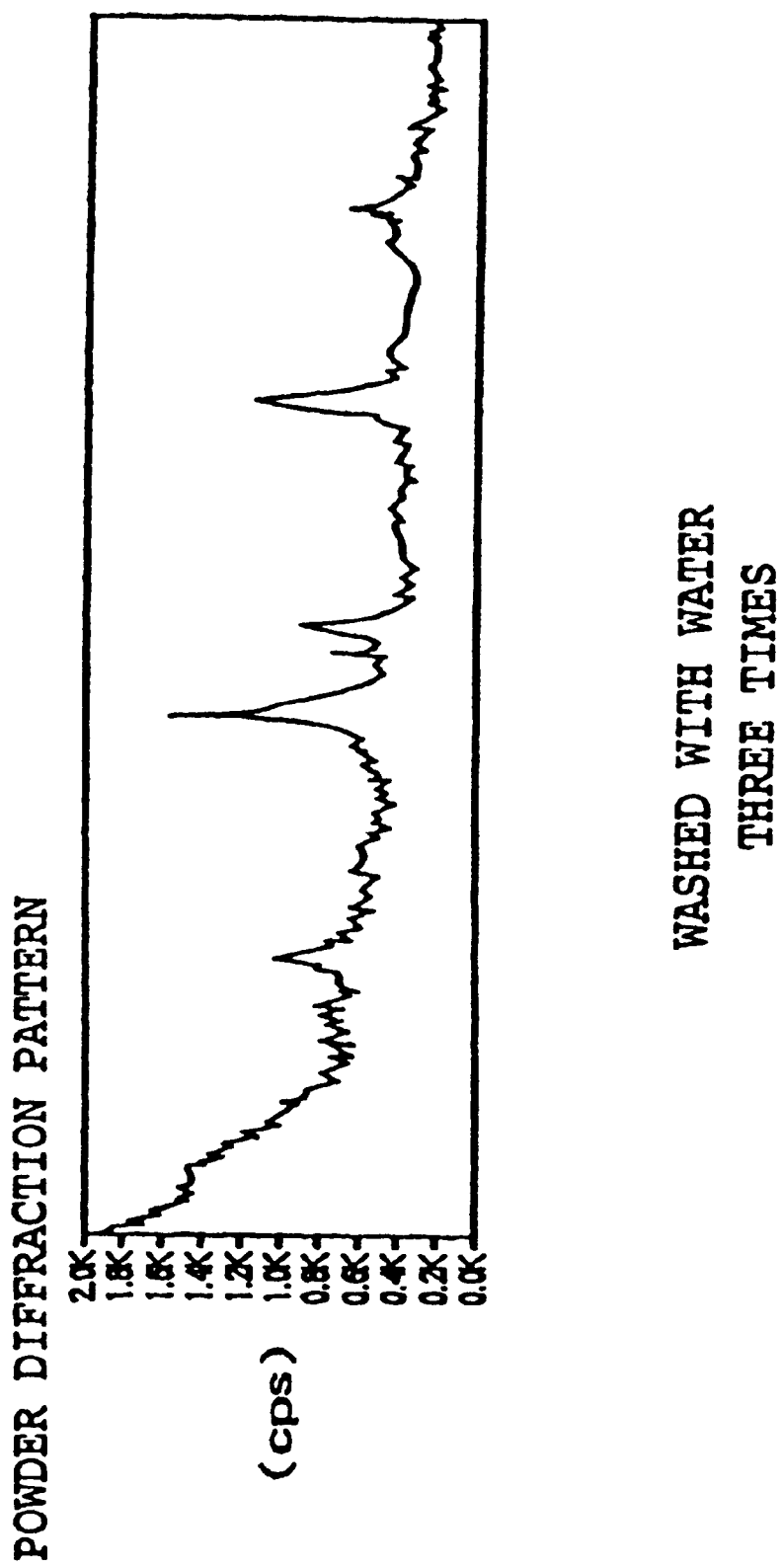

X-ray diffraction patterns of the $MnO_2$ thus obtained are shown in FIGS. 10(a)~10(c). The $MnO_2$ was analyzed by X-ray diffraction with a radiation source of Cu, a tube voltage of 50 KV, a tube current of 300 mA, and a monochromatic meter.

FIG. 10(a) shows an X-ray diffraction pattern produced when the solution is washed with water and filtered in two repeated cycles. As can be seen from FIG. 10(a), when the solution is washed with water and filtered in only two repeated cycles, a peak of $KMn_8O_{16}$ is recognized, and the specific surface area is of a small value of 94 $m^2$/g. FIG. 10(b) shows an X-ray diffraction pattern produced when the solution is washed with water and filtered in three repeated cycles. When the solution is washed with water and filtered in three repeated cycles, the specific surface area in-creases to a larger value of 131 $m^2$/g, but the $MnO_2$ remains crystalline. FIG. 10(c) shows an X-ray diffraction pattern produced when the solution is washed with water and filtered in four repeated cycles. When the solution is washed with water and filtered in four repeated cycles, as shown in FIG. 10(c), the specific surface area increases to a much larger value of 235 m$^2$/g, and the MnO$_2$ becomes amorphous.

Figure 11:
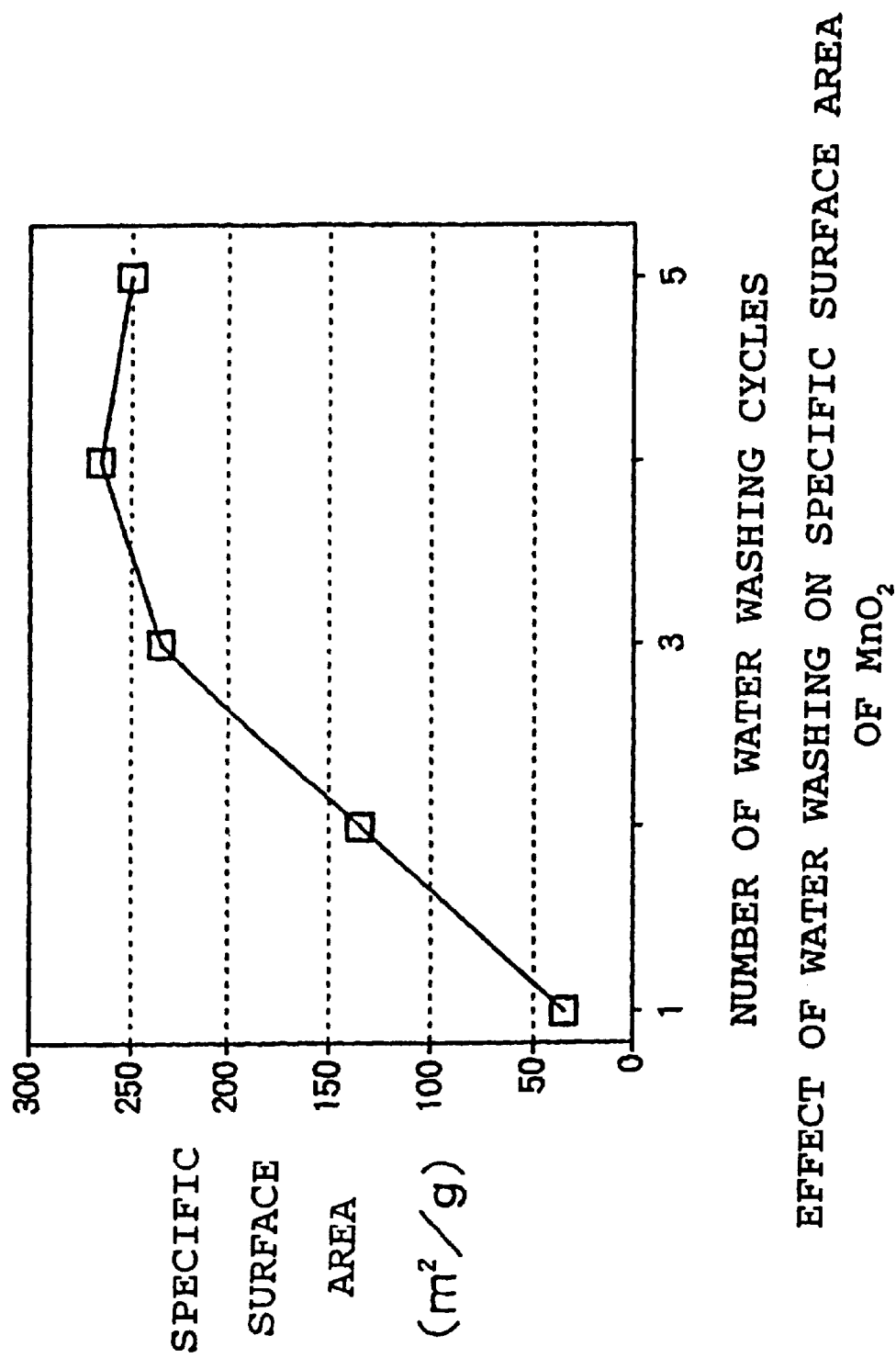
FIG. 11 is a graph showing the relationship between the specific surface area of $MnO_2$ and the number of water washing cycles.

FIG. 11 is a graph showing the relationship between the specific surface area of MnO$_2$ and the number of water washing cycles. Since the adsorbing capability increases as the specific surface area increases, the number of water washing cycles should preferably be four or more.

In the second step, the MnO$_2$ particles of substantially amorphous nature having a specific surface area of 200 m$^2$/g or higher, which have been produced in the first step, are mixed with CuO and activated carbon, and the MnO$_2$ particles and the CuO particles are carried on the activated carbon by a precipitation carrying process.

Figure 12:
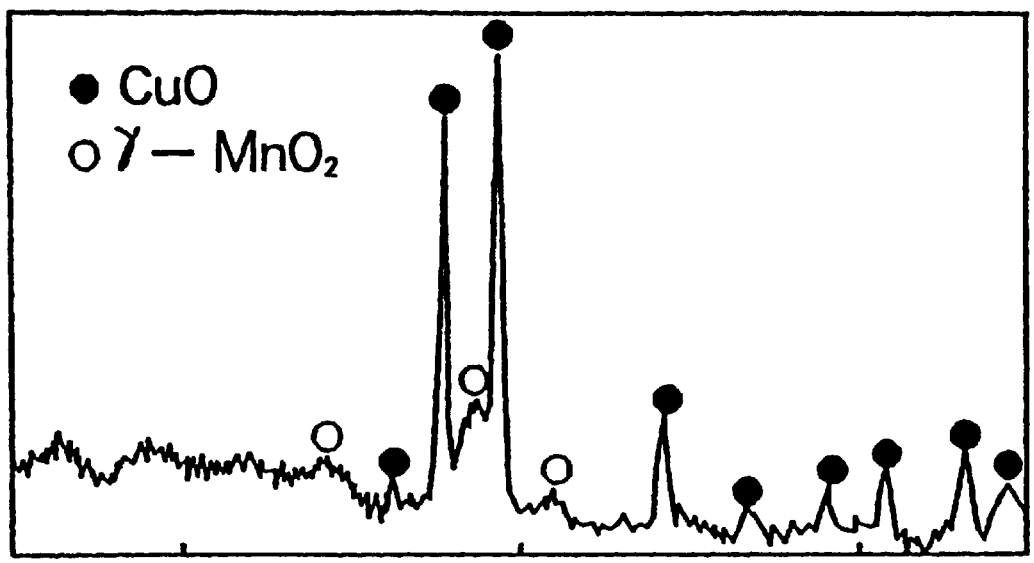
FIG. 12 is a diagram showing an XRD pattern of the deodorizer.

Specifically, for example 315 g of a pentahydrate of copper sulfate is dissolved into 1250 g of water, and then 150 g of a powder produced by grinding the MgO$_2$ described above with a mortar and 250 g of powdery activated carbon are dispersed in the solution, which is then stirred uniformly. Then, 3750 g of 1 N of caustic soda is introduced into the solution, which is thereafter stirred for 18 hours. Then, 5 liters of water is added to the mixture, which is filtered and washed with water in three repeated cycles, and then dried. The dried mass is crushed into about 500 g of a deodorizer in which fine MgO$_2$ and CuO crystal are dispersed and carried on the surface of activated carbon. It can be seen from FIG. 12 that fine MgO$_2$ and CuO crystal are dispersed and carried on the surface of activated carbon.

The activated carbon should preferably be coconut shell activated carbon having a specific surface area of 500 m$^2$/g or higher. The activated carbon may be in the form of a powder or fibers.

Figure 13:
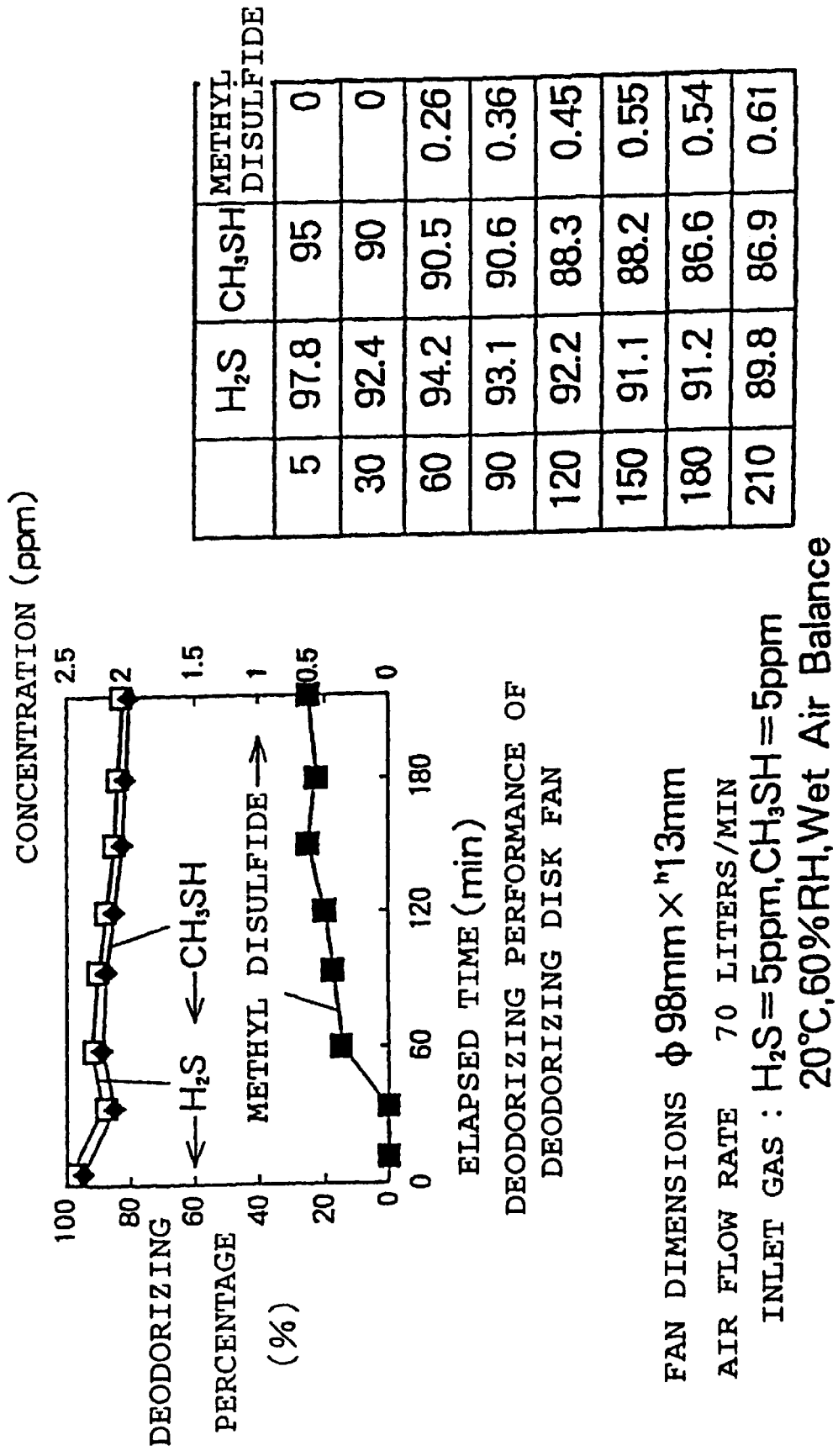
FIG. 13 is a graph showing experimental results of deodorizing effects of the deodorizing apparatus.

In order to confirm deodorizing effects of the deodorizing apparatus which incorporates the deodorizer according to the present invention, the apparatus shown in FIG. 9 was fabricated and experimented. The results of the experiment are shown in FIG. 13. The experiment was conducted with fan dimensions of 98 mm (diameter)×13 mm (height), an air flow rate of 70 liters/min., 5 ppm of H$_2$S at the air inlet, 5 ppm of CH$_3$SH at the air inlet, a temperature of 20° C., and a humidity of 60%.

It will be understood from FIG. 13 that when the deodorizing apparatus according to the present invention is used, the removal percentage of the original odors can be kept at 90% or higher for a long period of time, methyl disulfide (CH$_3$—S—S—CH$_3$) is generated in a small percentage of about 10%, and hence methyl trisulfide (CH$_3$—S—S—S—CH$_3$) is generated in a concentration of 0.1 ppm or less.

For human beings to clearly recognize that malodors have been removed, it is necessary that the odor intensity be reduced one step or more. Since the odor intensity is exponentially related to the odor concentration, reducing the odor intensity one step or more is equivalent to reducing the concentration of the original odors to 1/10 or less. This means that the removal percentage of the original odors should be 90% or more.

Deodorizing effects obtained when the above deodorizing apparatus was incorporated in the seats with a warm water cleaning capability of toilet bowls were evaluated. The results of the evaluation are shown in FIGS. 14(a) through 14(c).

Figure 14A:
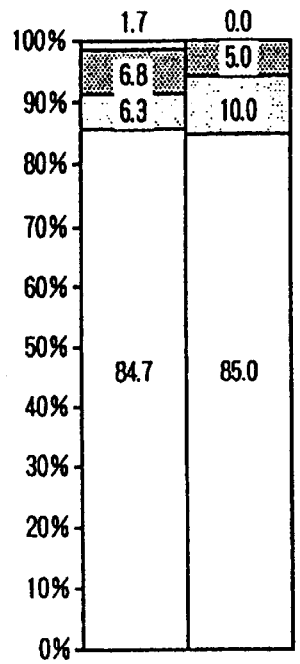
FIGS. 14(a)–14(c) are graphs showing comparative results of deodorizing effects achieved when the deodorizing apparatus according to the present invention and a conventional ozone deodorizing apparatus were incorporated in the seats with a warm water cleaning capability of toilet bowls (a seat with a built-in deodorizing fan and a seat with a built-in ozone deodorizing unit), FIG. 14(a) showing comparative results before the toilet bowls were used, FIG. 14(b) showing comparative results while the toilet bowls were being used, and FIG. 14(c) showing comparative results after the toilet bowls were used.
Figure 14B:
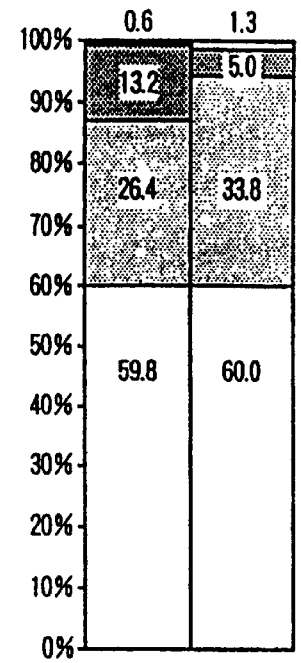
Figure 14C:
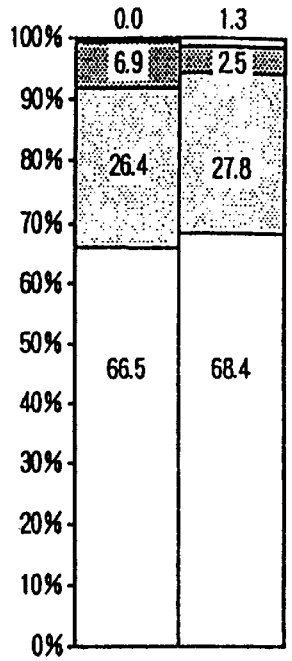

FIGS. 14(a) through 14(c) are graphs showing comparative results of questionnaires on deodorizing effects achieved when the deodorizing apparatus according to the present invention and a conventional ozone deodorizing apparatus were incorporated in the seats with a warm water cleaning capability of toilet bowls, i.e., a seat with a built-in deodorizing fan and a seat with a built-in ozone deodorizing unit. FIG. 14(a) shows comparative results before the toilet bowls were used. FIG. 14(b) shows comparative results while the toilet bowls were being used. FIG. 14(c) shows comparative results after the toilet bowls were used.

As shown in FIGS. 14(a) through 14(c), it has been confirmed that the deodorizing apparatus according to the present invention achieved substantially the same deodorizing effects as the conventional deodorizing apparatus.

According to the present invention, as described above, a polymerization reaction, an oxidization reaction, and an adsorption reaction are carried out simultaneously or stepwise at normal temperature for removing malodor components and preventing harmful products from being discharged.

Particularly, MnO$_2$ which has a strong oxidizing ability at normal temperature and CuO which assists the MnO$_2$ in its oxidizing action are combined with each other to allow the polymerization reaction and the oxidization reaction to be carried out efficiently, and powdery or fibrous activated carbon is used to effectively prevent harmful or malodorous products from being discharged.

MnO$_2$ particles which have a specific surface area of 200 m$^2$/g or higher and are substantially amorphous are selected, the weight ratios of MnO$_2$ particles and CuG particles are in the range from 8:2 to 4:6, and the proportion of the total amount of MnO$_2$ particles and CuO particles to activated carbon is in the range from 4:6 to 6:4 in terms of weight ratios. With these values, it is possible to effectively suppress the generation and discharge of methyl trisulfide.

According to the method of manufacturing a deodorizer, after a bivalent Mn compound and a septivalent Mn compound are reacted with each other, the reaction product is washed with water and filtered to produce amorphous MnO$_2$, and the amorphous MnO$_2$ and activated carbon are dispersed in an aqueous solution of a high concentration of copper salt such as CuSO$_4$ or Cu(NO$_3$)$_2$. In this manner, a deodorizer according to the present invention is manufactured.

Since a layer of the above deodorizer is formed on a fan of a deodorizing apparatus, the deodorizing apparatus is compact and requires no periodic replacement. When the deodorizing apparatus is incorporated in a toilet bowl, for example, the toilet bowl is given an increased value.

Although there have been disclosed what are at present considered to be the preferred embodiments of the invention, it will be understood by persons skilled in the art that variations and modifications may be made thereto without departing from the spirit or essence of the invention. The scope of the invention is indicated by the appended claims, rather than by the foregoing description.

What is claimed is:

1. A method for deodorizing malodor components, comprising the steps of:

reacting a first portion of first malodor components containing sulfur by a first oxidation;

removing a product of the first oxidation by bonding a metal component;

reacting a portion of second malodor components containing sulfur by a second oxidation;

removing a product of the second oxidation by bonding a metal component;

reacting a portion of remaining portions of the second malodor components by a first polymerization;

adsorbing a product of the first polymerization;

reacting another portion of the remaining portions of the second malodor components and a second portion of the first malodor components by a second polymerization with each other; and adsorbing a product of the second polymerization;

said steps being carried out simultaneously or stepwise at room temperature.

2. The deodorizing method according to claim 1, wherein: the first malodor components comprise hydrogen sulfide ($H_2S$) and said second malodor components comprise a $CH_3S$, said first oxidation reaction involves dehydrogenating the hydrogen sulphide ($H_2S$) to generate an HS group and an S group, and oxidizing the HS group to generate sulfuric acid ($H_2SO_4$), said step of removing the product of the first oxidation involves bonding the sulfuric acid ($CH_2SO_4$) to a metal, said second polymerization reaction involves polymerizing the S group with the $CH_3S$ group to generate at least one of methyl trisulfide ($CH_3$—S—S—S—$CH_3$) and methyl tetrasulfide ($CH_3$—S—S—S—S—$CH_3$), and said step of adsorbing the product of said second polymerization involves adsorbing the methyl trisulfide ($CH_3$—S—S—S—$CH_3$) and the methyl tetrasulfide ($CH_3$—S—S—S—S—$CH_3$) to the adsorbent.

3. The deodorizing method according to claim 2, wherein said adsorbent comprises at least one of powdery and fibrous activated carbon.

4. The deodorizing method according to claim 1, wherein: said second malodor components comprise methyl mercaptan ($CH_3SH$), said second oxidation reaction involves dehydrogenating the methyl mercaptan ($CH_3SH$) to generate a $CH_3S$ group, and oxidating a portion of $CH_3S$ group to generate methanesulphonic acid ($CH_3SO_3H$), said step of removing a product of the second oxidation involves bonding the methanesulphonic acid ($CH_3SO_3H$) to a metal, said first MRC polymerization reaction involves polymerizing another portion of the $CH_3S$ group with the $CH_3S$ group itself to generate methyl disulfide ($CH_3$—S—S—$CH_3$), said step of adsorbing a product of the first polymerization involves adsorbing at least a portion of the methyl disulfide ($CH_3$—S—S—$CH_3$) to said adsorbent, said second polymerization reaction involves polymerizing another portion of the $CH_3S$ group with S group of the first malodor components to generate at least one of methyl trisulfide ($CH_3$—S—S—S—$CH_3$) and methyl tetrasulfide ($CH_3$—S—S—S—S—$CH_3$), and said step of adsorbing a product of the second polymerization involves adsorbing at least a portion of the methyl trisulfide ($CH_2$—S—S—S—$CH_3$) or the methyl tetrasulfide ($CH_3$—S—S—S—S—$C_3$) to said adsorbent.

5. The deodorizing method according to claim 4, wherein said adsorbent comprises at least one of powdery and fibrous activated carbon.

6. A deodorizing method according to claim 1, wherein the first malodor components comprise hydrogen sulfide ($H_2S$) and the second malodor components comprise methyl mercaptan ($CH_3SH$);

said first oxidation reaction involves dehydrogenating hydrogen sulfide ($H_2S$) to generate an HS group and an S group and oxidizing the HS group to generate sulfuric acid ($H_2SO_4$), said second oxidation reaction involves dehydrogenating the methyl mercaptan ($CH_3SH$) to generate a $CH_3S$ group and oxidizing a portion of the $CH_3S$ group to generate methanesulfonic acid ($CH_3SO_3H$);

said second polymerization reaction involves polymerizing the S group with another portion of the $CH_3S$ group to generate at least one of methyl trisulfide ($CH_3$—S—S—S—$CH_3$) and methyl tetrasulfide ($CH_3$—S—S—S—S—$CH_3$), and said first polymerization reaction involves polymerizing still another portion of the $CH_3S$ group with the $CH_3S$ group itself to generate methyl disulfide ($CH_3$—S—S—$CH_3$);

said step of adsorbing the product of the first polymerization reaction involves adsorbing at least a portion of the methyl disulfide ($CH_3$—S—S—$CH_3$) to the adsorbent, and said step of adsorbing the product MRC the second polymerization involves adsorbing the methyl trisulfide ($CH_3$—S—S—S—$CH_3$) or the methyl tetrasulfide ($CH_3$—S—S—S—S—$CH_3$) to the adsorbent;

the step of removing the product of the first oxidation involves bonding the sulfuric acid ($H_2SO_4$) to a metal and the step of removing the product of the second oxidation involves bonding the methanesulfonic acid ($CH_3SO_3H$) to a metal.

7. The deodorizing method according to claim 6, wherein said adsorbent comprises at least one of powdery and fibrous activated carbon.

8. The deodorizing method according to claim 1, wherein said first and second oxidation reactions involve use of a metal oxide catalyst, wherein said adsorption steps involve use of activated carbon.

9. The deodorizing method according to claim 8, wherein said metal oxide catalyst comprises a first metal oxide for removing malodor components at room temperature by being bonded to the malodor components, and a second metal oxide for assisting the first metal oxide in a deodorizing action thereof.

10. The deodorizing method according to claim 9, wherein said adsorbent is in the form of a powdery or fibrous activated carbon, said first and second metal oxides are in the form of fine particles, said first metal oxide comprises $MNO_2$ particles having a substantially amorphous structure, and said first and second metal oxide particles are carried on surfaces of the adsorbent.

11. The deodorizing method according to claim 1, wherein said adsorbent comprises at least one of powdery and fibrous activated carbon.

12. The deodorizing method according to claim 1, wherein said method is for deodorizing malodor components in a toilet bowl.

* * * * *

UNITED STATES PATENT AND TRADEMARK OFFICE
CERTIFICATE OF CORRECTION

| | |
|---|---|
| PATENT NO. | : 6,207,106 B1 |
| DATED | : March 27, 2001 |
| INVENTOR(S) | : T. Kurokawa, C. Kobayashi, T. Tokumoto, M. Yamamoto, T. Tsuchida |

It is certified that error appears in the above-identified patent and that said Letters Patent is hereby corrected as shown below:

Column 1,
Lines 5-10, change
"TECHNICAL FIELD
This application is a division of application Ser. No. 08/737/648 filed Nov. 15, 1996 which is a 371 of PCT/JP96/00748 filed Mar. 22, 1996.
BACKGROUND OF THE INVENTION"
to
-- This application is a division of application Ser. No. 08/737,648 filed Nov. 15, 1996 (now U.S. Patent 6,010,666) which is a 371 of PCT/JP96/00748 filed Mar. 22, 1996.
BACKGROUND OF THE INVENTION
TECHNICAL FIELD --.

Column 2,
Line numbered between 24 and 25, change "is discussed" to -- as discussed --.

Column 4,
Line numbered between 40 and 41, change "S–CH,)," to -- S–CH$_3$), --;
Line numbered between 42 and 43, change "to promote dehydrogenated H$_2$S," to -- from the dehydrogenated H$_2$S to --.

Column 5,
Line 54, after "preferably" insert -- be --.

Column 6,
Line 35, after "example" insert a comma;
Line 63, change "in-creases" to -- increases --.

Column 7,
Line 16, after "example" insert a comma;
Line numbered between 18 and 19, change "MgO$_2$" to -- MnO$_2$ --;
Line numbered between 26 and 27, change "MgO$_2$" to -- MnO$_2$ --;
Line numbered between 28 and 29, change "MgO$_2$" to -- MnO$_2$ --.

Column 8,
Line 27, change "CuG" to -- CuO --;
Line numbered between 47 and 48, begin a new paragraph with "Although".

UNITED STATES PATENT AND TRADEMARK OFFICE
CERTIFICATE OF CORRECTION

PATENT NO. : 6,207,106 B1
DATED : March 27, 2001
INVENTOR(S) : T. Kurokawa, C. Kobayashi, T. Tokumoto, M. Yamamoto, T. Tsuchida It is certified that error appears in the above-identified patent and that said Letters Patent is hereby corrected as shown below:

Column 9,
Line numbered between 12 and 13, change "$CH_3S$," to -- $CH_3S$ group, --;
Line 38, delete "MRC";
Line 46, before "S group" insert -- an --;
Line 52, change "$CH_2$" to -- $CH_3$ --;
Line 53, change " S–S–S–S–S" to -- S–S–S–S --.

Column 10,
Line 22, change "MRC" to -- of --;
Line 37, change "wherein" to -- and --;
Line 49, change "$MNO_2$" to -- $MnO_2$ --.

Signed and Sealed this

Twenty-fifth Day of December, 2001

*Attest:*

*Attesting Officer*

JAMES E. ROGAN
*Director of the United States Patent and Trademark Office*